United States Patent
Forman et al.

[11] Patent Number: 6,129,704
[45] Date of Patent: Oct. 10, 2000

[54] PERFUSION BALLOON CATHETER HAVING A MAGNETICALLY DRIVEN IMPELLER

[75] Inventors: Michael R. Forman, Vadnais Heights; Jonathan S. Stinson, Plymouth, both of Minn.; Michael N. Helmus, Long Beach, Calif.

[73] Assignee: Schneider (USA) Inc., Plymouth, Minn.

[21] Appl. No.: 09/025,094

[22] Filed: Feb. 17, 1998

Related U.S. Application Data

[60] Provisional application No. 60/049,474, Jun. 12, 1997.

[51] Int. Cl.[7] ............................. A61M 29/00; A61M 1/00
[52] U.S. Cl. ............................. 604/96; 604/151; 604/915
[58] Field of Search ............................. 604/96, 102, 151, 604/915, 523; 600/16, 30; 623/3

[56] References Cited

U.S. PATENT DOCUMENTS

| | | | |
|---|---|---|---|
| 4,207,485 | 6/1980 | Silver | 310/104 |
| 4,382,245 | 5/1983 | Harrigan | 335/306 |
| 4,569,641 | 2/1986 | Falk et al. | 417/417 |
| 4,581,017 | 4/1986 | Sahota | 604/101 |
| 4,717,315 | 1/1988 | Miki et al. | 417/365 |
| 4,779,614 | 10/1988 | Moise | 600/16 |
| 4,909,252 | 3/1990 | Goldberger | 606/194 |
| 4,944,745 | 7/1990 | Sogard et al. | 606/194 |
| 5,002,531 | 3/1991 | Bonzel | 604/96 |
| 5,004,454 | 4/1991 | Beyar et al. | 600/30 |
| 5,046,503 | 9/1991 | Schneiderman | 128/692 |
| 5,092,844 | 3/1992 | Schwartz et al. | 604/151 |
| 5,108,370 | 4/1992 | Walinsky | 604/96 |
| 5,163,910 | 11/1992 | Schwartz et al. | 604/151 |
| 5,181,911 | 1/1993 | Shturman | 604/96 |
| 5,226,888 | 7/1993 | Arney | 604/96 |
| 5,232,445 | 8/1993 | Bonzel | 604/96 |
| 5,232,446 | 8/1993 | Arney | 604/96 |
| 5,248,245 | 9/1993 | Behnke et al. | 417/366 |
| 5,252,159 | 10/1993 | Arney | 156/169 |
| 5,253,986 | 10/1993 | Bond et al. | 417/420 |
| 5,318,535 | 6/1994 | Miraki | 604/102 |
| 5,366,506 | 11/1994 | Davis | 623/12 |
| 5,368,566 | 11/1994 | Crocker | 604/101 |
| 5,370,617 | 12/1994 | Sahota | 604/102 |
| 5,377,816 | 1/1995 | Deligi et al. | 198/619 |
| 5,383,890 | 1/1995 | Miraki et al. | 606/194 |
| 5,395,333 | 3/1995 | Brill | 604/101 |
| 5,405,383 | 4/1995 | Barr | 623/3 |
| 5,433,706 | 7/1995 | Abiuso | 604/96 |
| 5,456,134 | 10/1995 | Bouwer et al. | 74/490.09 |
| 5,466,932 | 11/1995 | Young et al. | 250/289 |
| 5,469,035 | 11/1995 | Lowrance | 318/568.1 |
| 5,470,314 | 11/1995 | Walinsky | 604/96 |
| 5,472,577 | 12/1995 | Porter et al. | 204/1.11 |
| 5,484,411 | 1/1996 | Inderbitzen et al. | 604/96 |
| 5,499,909 | 3/1996 | Yamada et al. | 417/384 |
| 5,501,582 | 3/1996 | Gautier et al. | 417/420 |
| 5,501,667 | 3/1996 | Verduin, Jr. | 604/96 |
| 5,527,159 | 6/1996 | Bozeman, Jr. et al. | 417/45 |
| 5,529,465 | 6/1996 | Zengerle et al. | 417/413.2 |
| 5,545,135 | 8/1996 | Iacob et al. | 604/96 |
| 5,589,721 | 12/1996 | Han et al. | 310/90.5 |
| 5,607,292 | 3/1997 | Rao | 417/417 |
| 5,609,602 | 3/1997 | Machemer et al. | 606/171 |
| 5,762,599 | 6/1998 | Sohn . | |
| 5,911,685 | 6/1999 | Siess et al. | 600/16 |
| B1 4,762,129 | 7/1991 | Bonzel | 606/194 |

FOREIGN PATENT DOCUMENTS

| | | |
|---|---|---|
| 9528983 | 11/1995 | WIPO . |
| 9529716 | 11/1995 | WIPO . |

*Primary Examiner*—Glenn K. Dawson
*Assistant Examiner*—Michael Hayes
*Attorney, Agent, or Firm*—Todd P. Messal

[57] ABSTRACT

A balloon catheter having a perfusion lumen communicating with a blood vessel, and a magnetically driven impeller disposed in the perfusion lumen to increase blood flow through the catheter and the arteries.

17 Claims, 13 Drawing Sheets

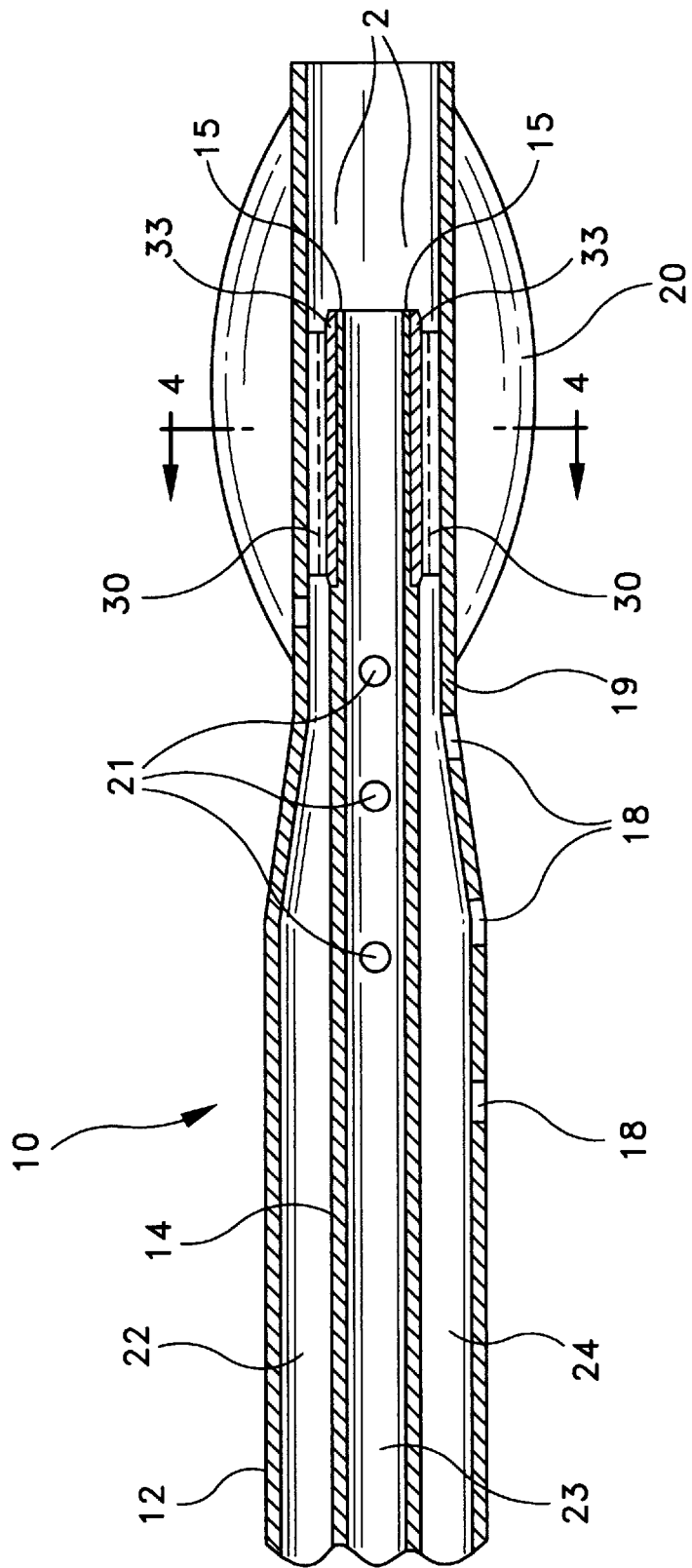

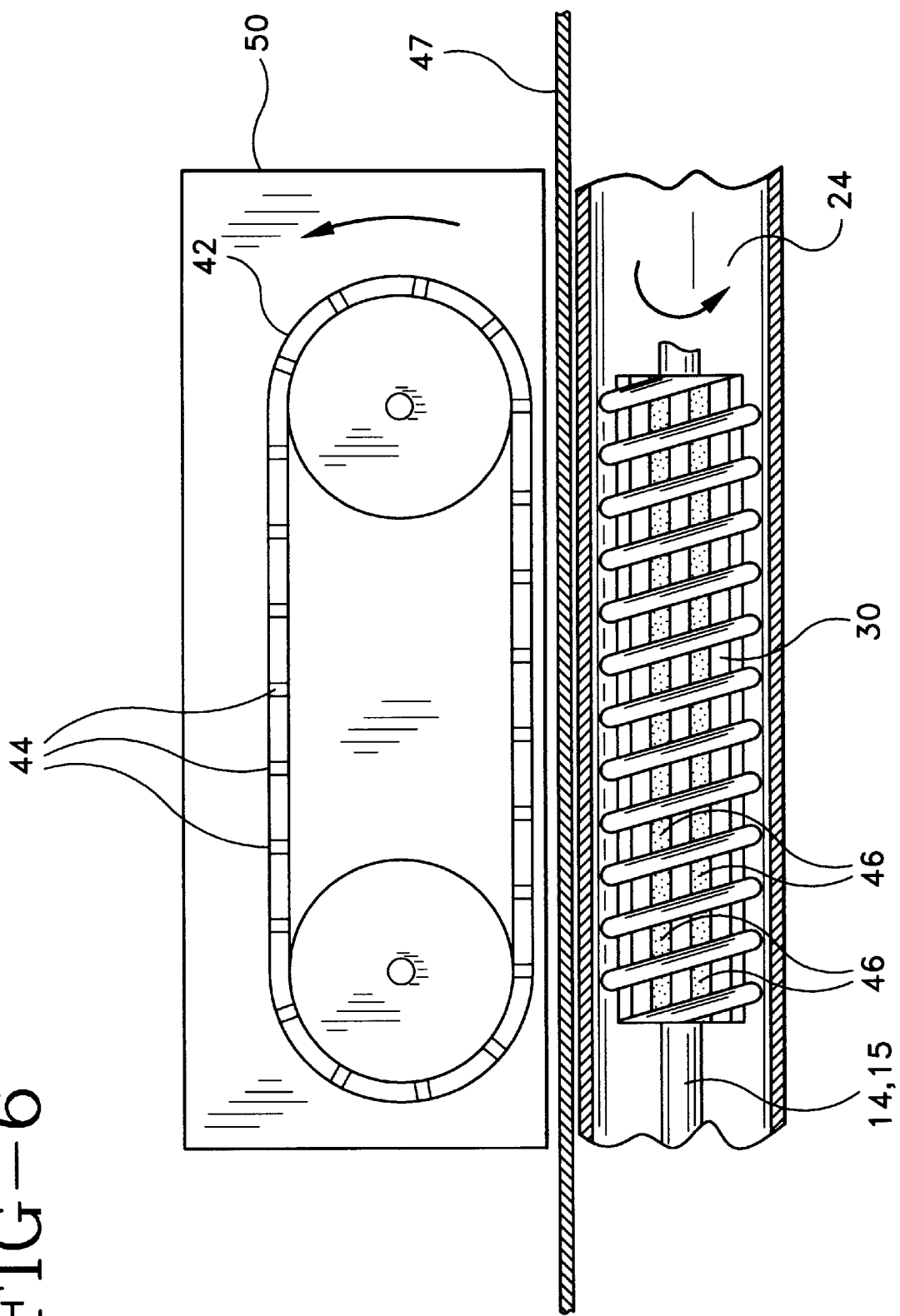

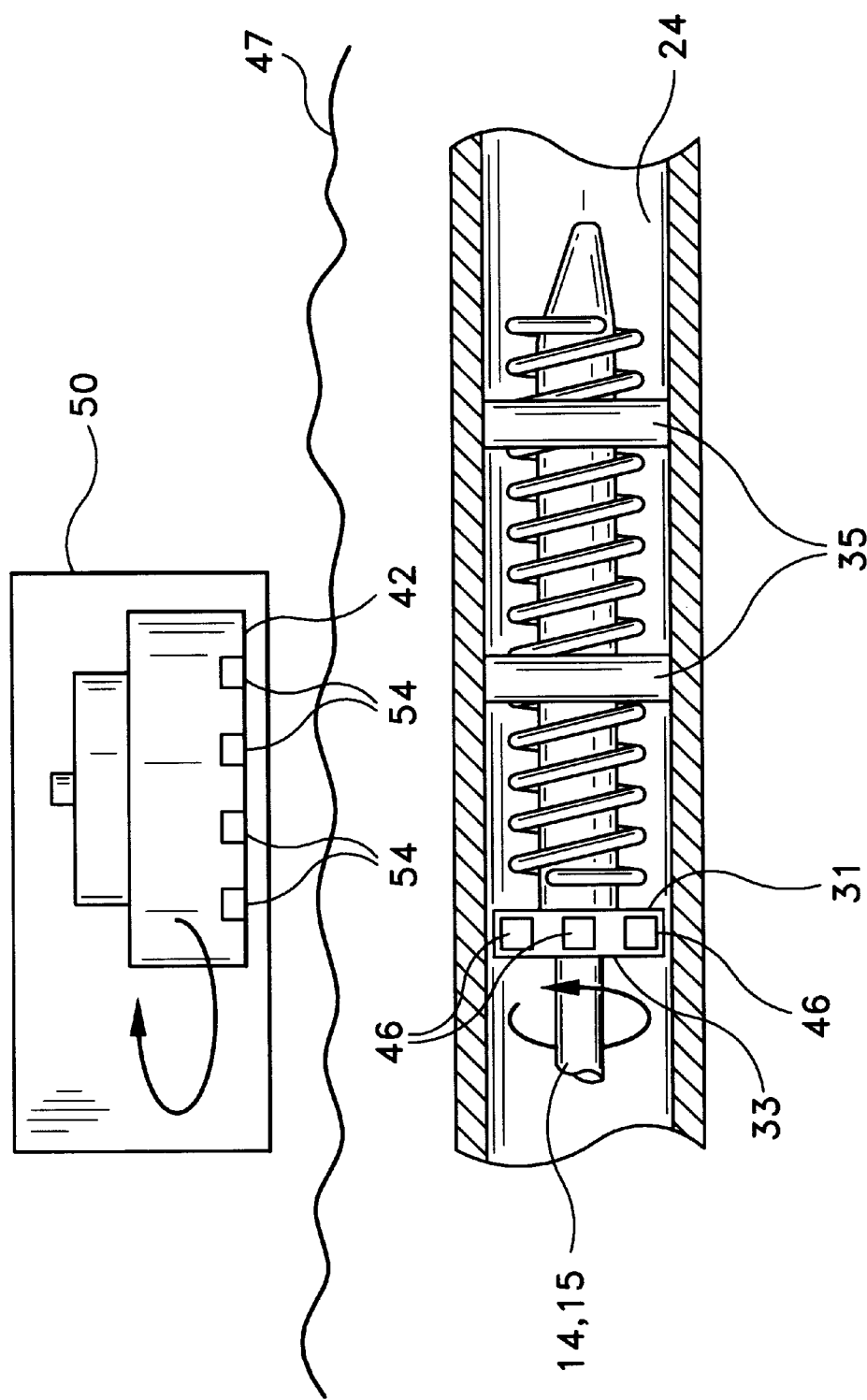

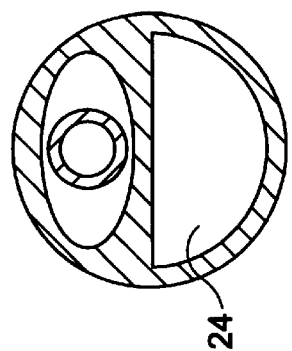
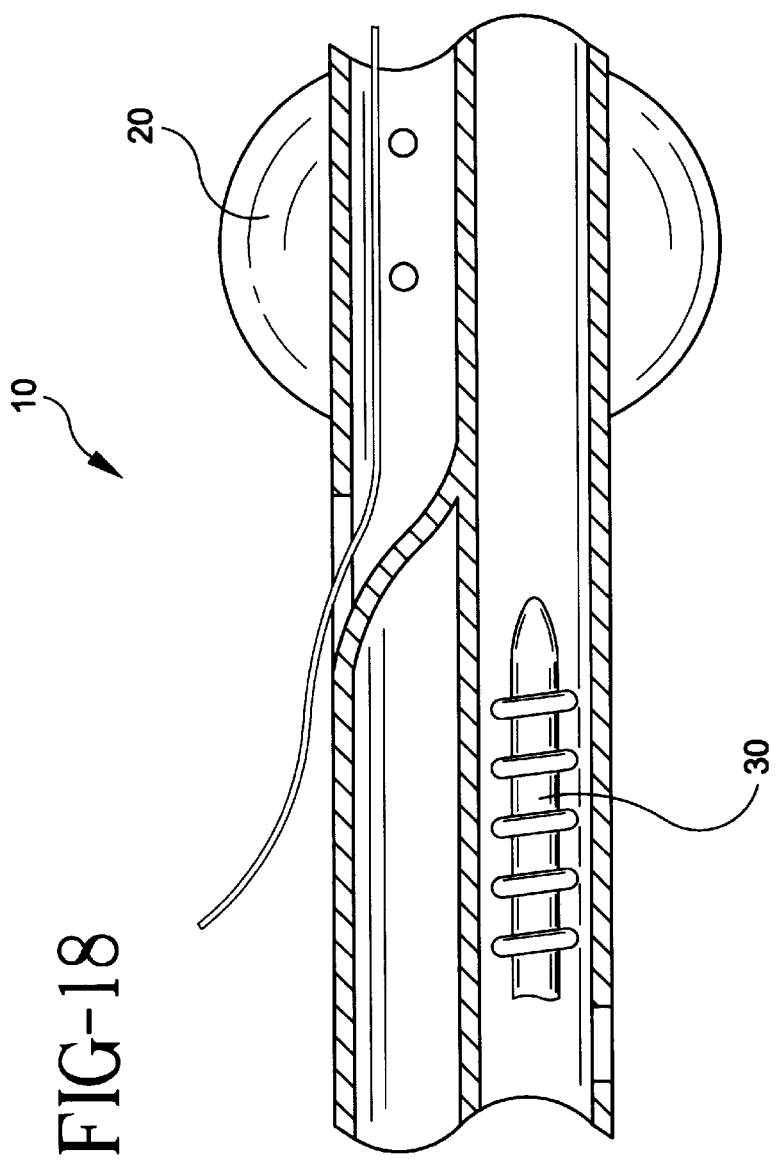

PERFUSION BALLOON CATHETER HAVING A MAGNETICALLY DRIVEN IMPELLER

BACKGROUND OF THE INVENTION

This application claims the benefit of United States Provisional patent application, Ser. No. 60/049,474, entitled PERFUSION BALLOON CATHETER, filed Jun. 12, 1997.

This invention relates generally to an active perfusion balloon catheter, particularly, a catheter having a magnetically driven impeller to facilitate blood flow. Active perfusion balloon catheters may be used in percutaneous transluminal coronary angioplasty and in other medical procedures to maintain blood flow through body lumens.

The need for active perfusion catheters has become more desirable with advances in micro-surgery, neuro-surgery, interventional neuroradiology, minimally invasive coronary arterial bypass procedures, intravascular radiation for prevention of restenosis after angioplasty and stenting, and conventional angioplasty procedures.

Various perfusion catheters are known in the art including WO 95/28983; and U.S. Pat. Nos. 4,581,017; 4,909,252; 4,944,745; 5,092,844; 5,163,910; 5,370,617; 5,405,383; and 5,501,667. Various catheters are disclosed in U.S. Pat. Nos. B1 4,762,129; 5,002,531; and 5,232,445. Magnets, magnetic coupling forces, and pump systems are disclosed in U.S. Pat. Nos. 4,207,485; 4,382,245; 4,569,641; 4,717,315; 5,248, 245; 5,253,986; 5,609,602; 5,377,816; 5,456,134; 5,589, 721; and 5,501,582. A magnetically coupled implantable medical device is disclosed in WO 95/29716.

All documents cited herein, including the foregoing, are incorporated herein by reference in their entireties for all purposes.

SUMMARY OF THE INVENTION

Accordingly, there is a need for catheters having perfusion to maintain blood flow through body lumens during medical procedures. The active perfusion catheter of the present invention incorporates a magnetically driven impeller that advantageously provides blood flow to coronary arteries temporarily blocked during balloon dilatation. The catheter shafts and components are made of plastics, polymers, or metals known in the art.

The catheter has one or more passages for blood to reach the opposite side of the treatment area during balloon dilatation. Blood flow may be through an active perfusion lumen where aperture holes and a miniature impeller having magnetic coupling properties actively facilitate fluid movement. Impeller rotation is implemented by an external magnetic force. The external magnetic drive system rotates and causes a corresponding rotation of the impeller disposed in the catheter. The impeller may be disposed on a shaft and rotate on bearings to minimize frictional forces.

Blood may also flow through a passive perfusion lumen where aperture holes and system pressure allows blood to flow through the guidewire lumen to regions proximal or distal of the balloon. Passive perfusion may occur through a guidewire lumen as blood enters through one or more apertures in the wall of the shaft. The apertures are located proximal of the balloon, and system pressure drives blood longitudinally through additional perfusion openings or apertures. The active and passive perfusion systems may be used in combination.

The external magnetic drive system may be contained in an enclosure and include an electrical or battery power source. The enclosure provides containment and protection of the drive system and may be placed on the patients body adjacent an area in the body where the impeller of the catheter is disposed.

The drive system includes a magnet or magnetic surface which rotates about an axis. The drive system may be powered by a motor and include an on-off switch, variable speed control, and various control systems to measure and monitor the rotation of the magnetic surface and the corresponding blood flow through the catheter. Also, controls may measure the strength of the magnetic coupling of the magnetic surfaces, and the rotational speed of the impeller. The magnetic drive system includes magnetic flux properties capable of transmitting sufficient magnetic forces to the magnetic impeller and for magnetic coupling to occur.

The impeller may be located in a portion of the catheter intended to be disposed in the ascending aorta which generally allows the catheter to have a larger impeller. Accordingly, the impeller is preferably located about six inches proximal of the balloon.

In sum, the invention relates to a perfusion balloon catheter including a first shaft having proximal and distal portions, a wall, one or more first apertures through the wall, a balloon disposed on the shaft distal of the first apertures, an inflation lumen in communication with the balloon, and a perfusion lumen in communication with the first apertures. At least one impeller is disposed in the perfusion lumen. The impeller has a predetermined shape and one or more magnets disposed thereon. The magnets magnetically couple with a magnetic source causing rotation of the impeller. Rotation of the impeller may convey fluid through the perfusion lumen. The perfusion balloon catheter may further include a second shaft disposed in the first shaft, through the impeller, and extend distal thereof. The second shaft has proximal and distal portions and a wall. The wall has one or more apertures in the distal portion of the second shaft, and one or more apertures distal of the impeller. A perfusion lumen is disposed in the second shaft between the apertures and is in communication therewith. The impeller may be located distal of the first apertures. The impeller may be disposed under a portion of the balloon. The impeller may be made of metal, ceramic, or polymeric material. The impeller may include at least one spiral-shaped groove. The impeller may include one rib, thread, or screw. The impeller may operate like an archimedes screw. The perfusion balloon catheter may further include an external magnetic drive system adapted to provide a magnetic field to a vicinity of the magnets on the impeller. The external magnetic drive system may be powered by a source including a battery, electricity, magnetic coupling, or combination thereof. The impeller may further include a plurality of magnets disposed thereon to collectively form a continuous spiral magnet. The impeller may include a plurality of magnets disposed side-by-side to form a generally continuous magnetic thread. Each magnetic thread has an opposite magnetic polarity at its outer extremity to its adjacent magnetic thread. The impeller rotates by exposing at least one magnetic thread to successive magnetic drive magnets of the opposite polarity upon rotation of the magnetic drive system. Successive magnetic coupling between the magnetic threads and the successive magnets on the magnetic drive system causes rotation of the impeller. The perfusion balloon catheter may further include an external magnetic drive system including a magnetic surface adapted to generate a magnetic field to one or more magnets disposed on a component connected to the impeller causing a magnetic coupling and rotation of the impeller.

The invention also relates to a perfusion catheter system including a catheter having proximal and distal ends, one or more lumens, and an elongated impeller having proximal and distal ends disposed in one of the lumens. One or more magnets are disposed on the impeller or a component connected to the impeller. The impeller magnetically couples with a magnetic drive system, rotates, and moves fluid through the catheter. The catheter is disposed in a body lumen for treatment. The magnetic drive system is external to the catheter and has one or more magnets that rotate about an axis and convey a magnetic field to the one or more magnets disposed on the impeller. The impeller may move fluid in a predetermined direction when rotated.

The invention also relates to a method of actively perfusing blood through a catheter including inserting a shaft into an artery. The shaft has proximal and distal portions, a wall, one or more first and second apertures in the wall, and at least one perfusion lumen disposed therein between the first apertures and the second apertures and in communication with the first and second apertures. The perfusion lumen has at least one elongated magnetic member rotatably disposed therein. Rotating the member using an external magnetic force causes the impeller to convey fluid into one of the first or second apertures, through the perfusion lumen, and out the other of the first or second apertures upon application of a magnetic force.

The invention also relates to a perfusion catheter system including a drive system including an elongated shaft having at least one magnetic surface including one or more first magnets disposed thereon. The magnetic surface adapted to rotate and be disposed on or adjacent a body surface. The catheter is less than about 15 French in size, has proximal and distal ends, one or more lumens longitudinally disposed therein, one or more supports mounted in the lumen, and an elongated impeller having one or more second magnets disposed thereon. The drive system is adapted to rotate causing successive magnetic coupling between the first magnets and the second magnets and rotation of the impeller. The first magnets may be magnetically attracted to the second magnets of the opposite polarity and magnetically couple. The rotation of the magnetic surface may expose the second magnets to different first magnets of the opposite polarity which are disposed further along the length of the magnetic surface such that the second magnets are magnetically coupled to different first magnets as the shaft rotates causing the impeller to rotate and fluid to move in the catheter.

The invention also relates to a method of actively perfusing blood through a catheter comprising the steps of inserting a shaft into a body lumen. The shaft having proximal and distal portions, a wall, one or more first apertures in the wall, and at least one perfusion lumen disposed distal of the first apertures and being in communication therewith. The perfusion lumen has at least one impeller disposed rotatably therein. The impeller has one or more magnets disposed thereon and is adapted to rotate and convey blood through one of the first apertures and through the perfusion lumen upon application of a magnetic force thereto; applying a magnetic field to the impeller from external the body lumen; and causing magnetic coupling and rotation of the impeller using the magnetic field. The method may include using an impeller including a plurality of magnets disposed generally side-by-side to form a generally continuous magnetic thread. Each magnetic thread has an opposite magnetic polarity at its outer extremity to its adjacent magnetic thread. The method may further include the step of exposing at least one magnetic thread to successive magnetic drive magnets of the opposite polarity by rotating the magnetic drive so that successive magnetic coupling between the magnetic thread and the successive magnetic drive magnets rotates the impeller.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTION OF THE DRAWINGS

FIG. 2 illustrates a side view of another embodiment of the perfusion balloon catheter;

FIG. 6 illustrates a view of an embodiment of an external magnetic drive system disposed over an impeller in a catheter in a body lumen;

FIG. 8 illustrates a view of an embodiment of an external magnetic drive system disposed over an impeller in a catheter in a body lumen;

FIG. 18 illustrates a coaxial to bitumen embodiment of the perfusion catheter having lumens, aperture, impeller, balloon, and guidewire; and FIG. 19 illustrates a cross-sectional view of the catheter of FIG. 18 illustrating a contrast lumen, guidewire lumen and perfusion lumen.

DETAILED DESCRIPTION OF THE INVENTION

Figure 1:
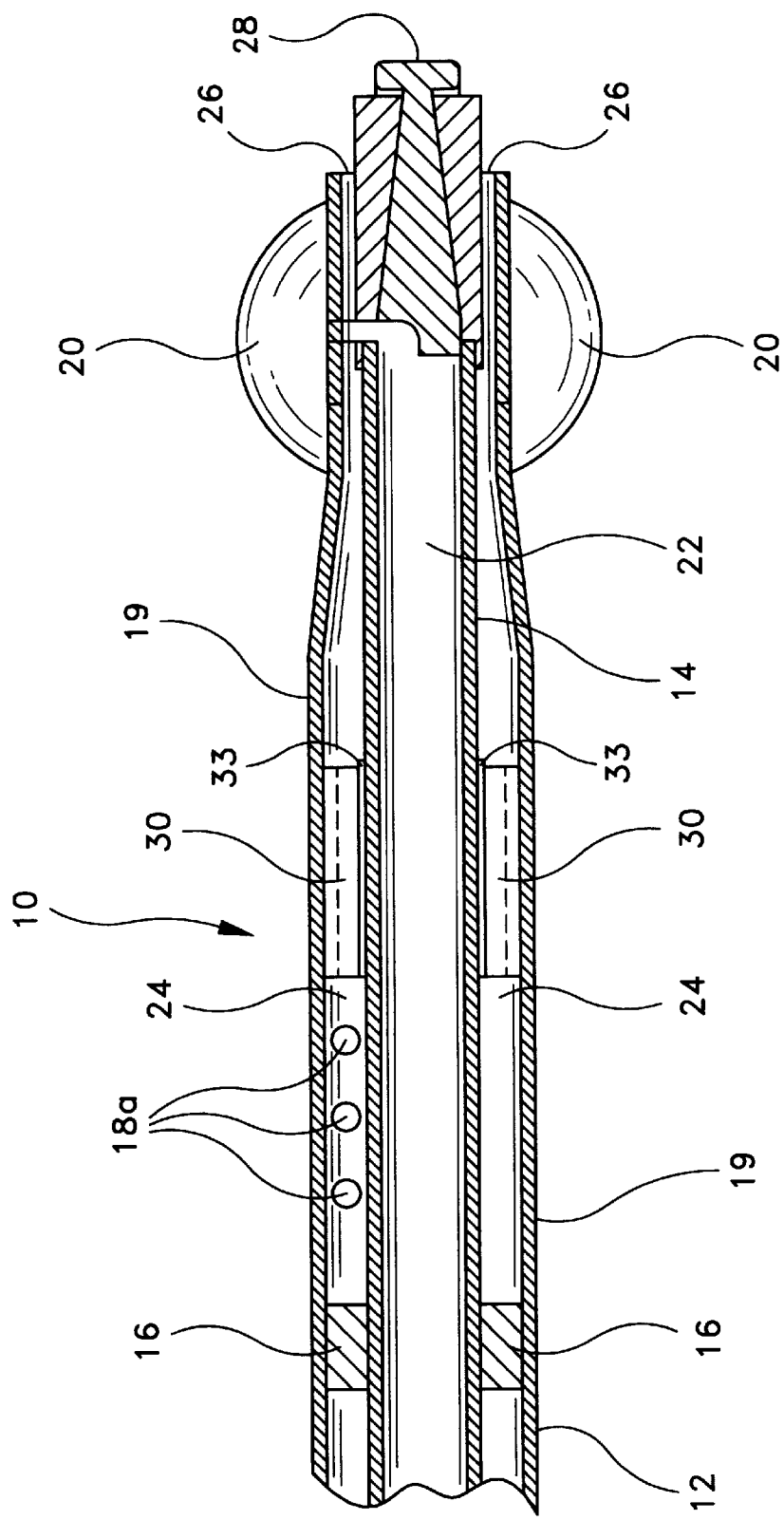
FIG. 1 illustrates a side view of a perfusion balloon catheter.

The perfusion balloon catheter 10 may include rapid-exchange, over-the wire, or fixed wire embodiments. Reference is made to FIGS. 1 and 2 which illustrate the distal portion of two embodiments of the perfusion balloon catheter 10 having active perfusion, passive perfusion, or combinations of both characteristics. Various sizes and embodiments of the catheter 10 in about the 3 French to 34 French range are envisioned. The impeller 30 may be located proximal of the balloon 20 which would allow a relatively larger diameter impeller 30 disposed in the catheter 10.

FIG. 1 illustrates the distal portion of a catheter 10 having an outside shaft 12 and an inside shaft 14. Secured between the outside shaft 12 and the inside shaft 14 may be a flow block 16 to prevent blood flow to the proximal portion of the catheter 10. One or more proximal apertures 18 are located proximal of the impeller 30 and extend through the wall 19 of the outside shaft 12 to allow blood to flow to the active perfusion lumen 24 and through the impeller 30. The impeller 30 is disposed on bearings 33 and rotates when successive magnetic or electromagnetic forces are applied and after successive magnetic coupling occurs. Successive magnetic coupling provides sufficient torque to rotate the impeller 30 at a desired speed to move the blood through the catheter 10. For example, as the impeller 30 is rotated, blood may be forced distally through the impeller 30 to a distal perfusion opening 26 or a distal aperture 18 (not shown) located distal of the balloon 20. An inflation lumen 22 is disposed in the catheter 10 which communicates with the balloon 20. The inflation lumen 22 may run through the shaft of the impeller 30, or the inflation lumen 22 may be a dedicated lumen extruded in the catheter 10. A tip 28 may be connected to one of the shafts 12, 14 at the distal end of the catheter 10.

FIG. 2 illustrates an over-the-wire embodiment of the catheter 10 including an outside shaft 12 and an inside shaft 14. An inflation lumen 22 is disposed in the catheter 10 and communicates with the balloon 20. Secured between the outside shaft 12 and the inside shaft 14 may be a flow block 16 (not shown). One or more proximal apertures 18 are located proximal of an impeller 30 and extend through the wall 19 and allow blood to flow into the active perfusion lumen 24 and into the impeller 30 or into the guide lumen 23. When successive magnetic forces are applied to the impeller 30, rotation occurs, and blood or fluid is moved through passages and the catheter 10. Apertures 21 are provided through the wall of the inside shaft 14 into the guide lumen 23. A tube 15 made of a material such as Nitinol, having an inside diameter dimension of about 0.013 inches and an outside diameter of about 0.016 inches may extend distally from the distal end of the inside shaft 14 for a length of about 0.500 inches. The impeller 30 may be disposed on the tube 15 and bearings 33. Preferably, frictional forces are minimal between the impeller 30 and bearings 33, and the impeller 30 and the catheter shaft 12. The impeller 30 has threads which force fluid in a predetermined direction upon rotation. The size and pitch of the threads provide a predetermined flow at a certain rotational speed.

Figure 3:
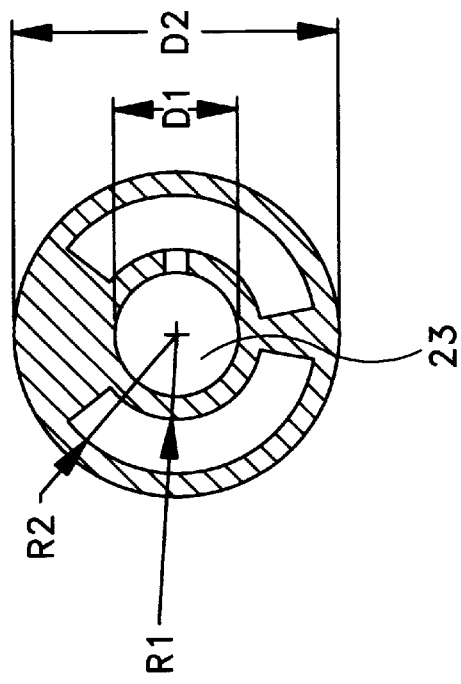
FIG. 3 illustrates a cross-sectional view of an embodiment of the catheter.

FIG. 3 illustrates a cross-sectional view of an embodiment of a trilumen catheter 10. In one embodiment, radius R1 is about 0.011 inches, radius R2 is about 0.020 inches; diameter D1 is about 0.016 inches; and diameter D2 is about 0.047 inches.

Figure 4:
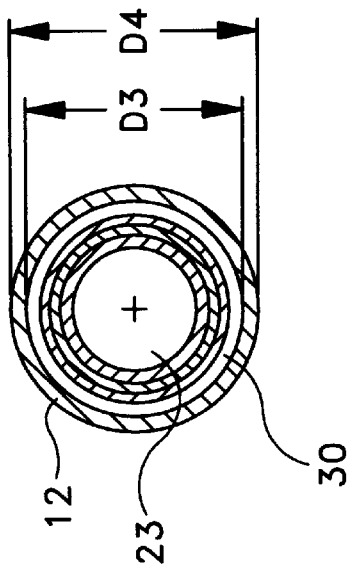
FIG. 4 illustrates a cross-sectional view (excluding balloon) taken along the line 4—4 of FIG. 2.

FIG. 4 illustrates a cross-sectional view of a trilumen catheter 10a taken along line 4—4 in FIG. 2. In one embodiment, diameter D3 is about 0.031 inches, and diameter D4 is about 0.037 inches.

Figure 5:
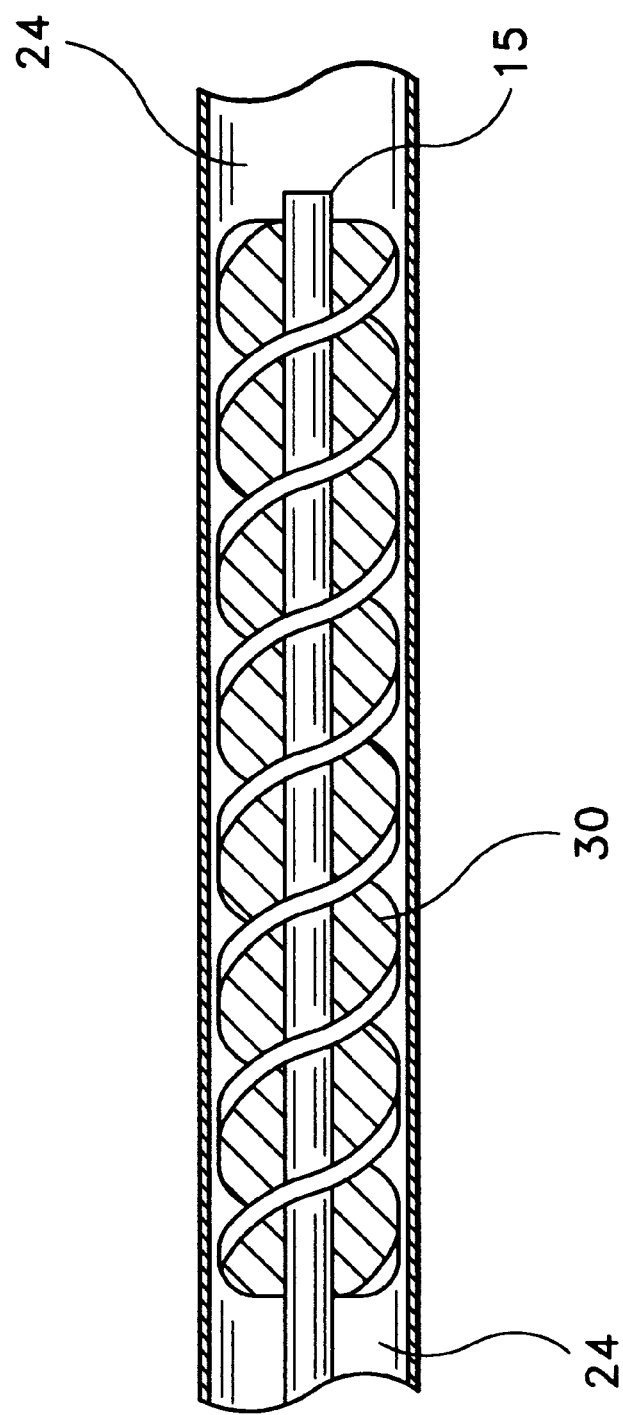
FIG. 5 illustrates a view of an embodiment of an impeller disposed in a catheter lumen.

FIG. 5 illustrates an embodiment of an impeller 30 having a helical design which is disposed in the perfusion lumen 24 of the catheter 10. The impeller 30 may be an archimedes screw design with spiral threads or screw shapes. The impeller 30 may include a tube bent spirally around an axis or include a broadthread. The impeller 30 may be made of metal, ceramic, or polymeric materials and be machined or molded to a desired shape. The impeller 30 is preferably made of a flexible polymeric material adapted for tortuous passage through arteries. The shaft 14 or tube 15 may have protrusions (not shown) which allow rotation, but prevent substantial longitudinal displacement of the impeller 30. The impeller 30 may also have adjustments (not shown) to prevent rotation in a certain direction.

Figure 7A:
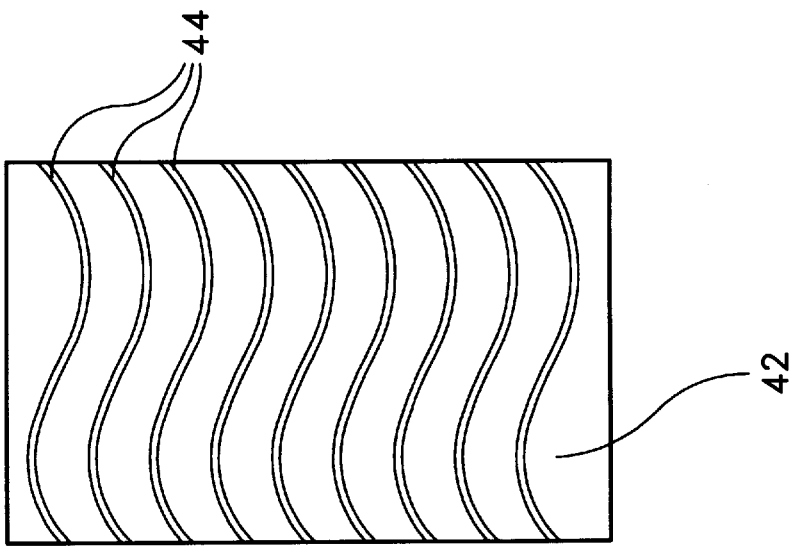
FIGS. 7a–c illustrates views of several embodiments of magnetic surface patterns of the external magnetic drive system of FIG. 6.
Figure 7B:
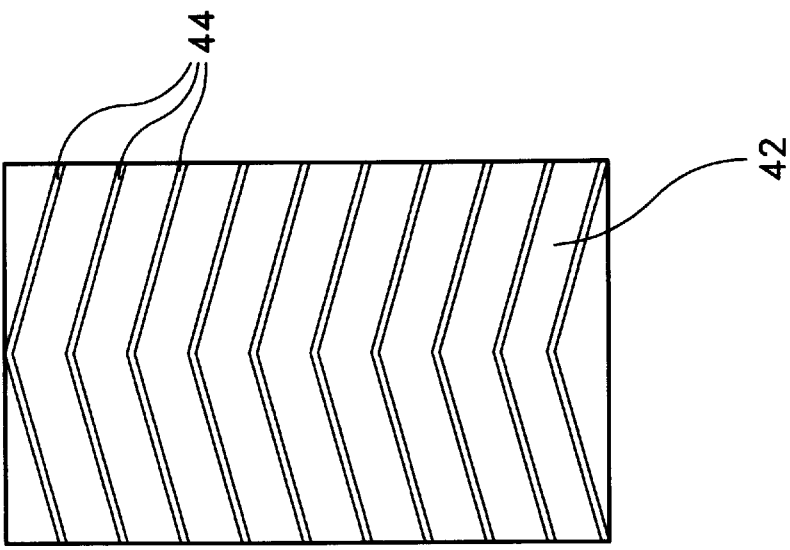
Figure 7C:
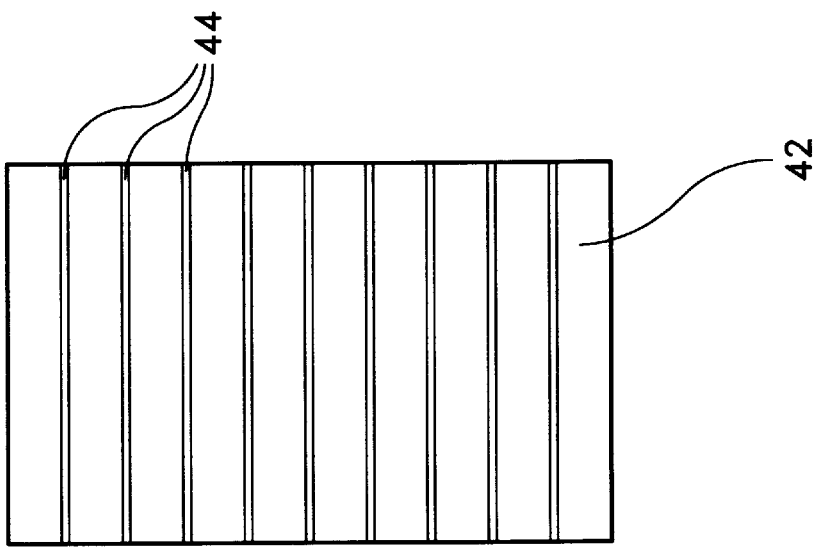
Figure 9:
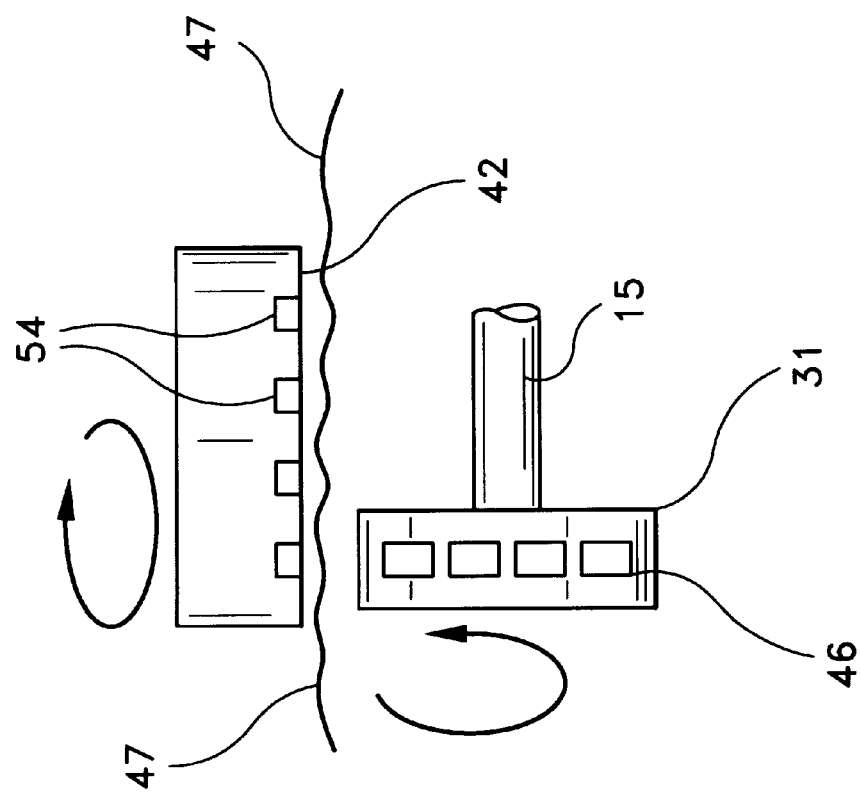
FIG. 9 illustrates a view of an embodiment of an external magnetic drive system disposed over a catheter component in a body lumen.

Reference is made to FIG. 6 showing an embodiment of an external magnetic drive system 50 which includes a power source (not shown) and a magnetic surface 42 having magnets 44 disposed therein in predetermined patterns. The magnetic drive system 50 is shown disposed over an embodiment of the impeller 30 in a catheter 10, in a body lumen, under a body surface 47. Various patterns and sizes of magnetic polarity are incorporated on or in the magnetic surface 42 for magnetic coupling. Certain patterns and sizes such as shown in FIGS. 7a–7c may assist with the alignment of the lead angle of the magnetic surface 42 to the lead angle of the magnets 46. As shown in FIGS. 8 and 9, the magnetic surface 42 magnetically couples with magnets 46 disposed on he component 31 which is rotatably connected to the impeller 30. The impeller 30 ay be mounted on a metal support shaft 15 or on shaft 14. Supports 35 may be used to support portions of the impeller 30.

In operation, the magnetic surface 42 is activated and rotated in a linear or rotational motion on a patients body in the vicinity of the impeller 30 and the magnetic forces are used to provide rotational motion of the impeller 30. Rotation of the magnetic surface 42 creates a magnetic field which causes magnets 46 in the catheter 10 to attempt to orient with the magnets 44, 54 of the magnetic surface 42. The successive attempts of the magnets 46 to orient with magnets 44, 54 causes the impeller 30 to rotate. The magnets 44 54 are of sufficient magnetic strength or flux to cause the impeller 30 to rotate. When the magnetic surface 42 is deactivated or removed from the patient's body, the successive magnetic couplings no longer occur, and rotation of the impeller 30 stops. Accordingly, fluid may be drawn through the various apertures into the perfusion lumen 24 and out the other apertures. The magnetic surface 42 is preferably rotated in a plane parallel to the longitudinal axis of the impeller 30.

Figure 10A:
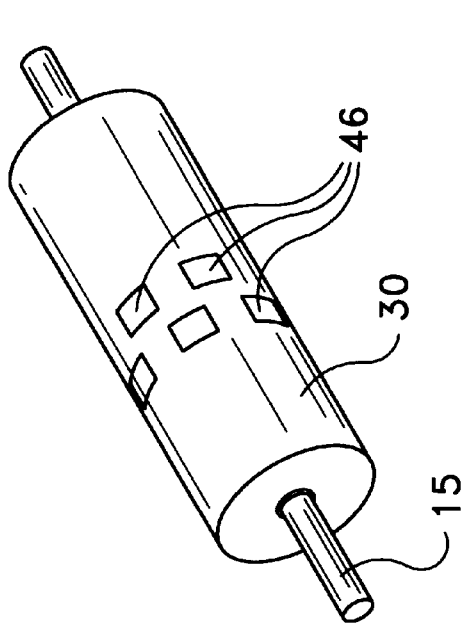
FIGS. 10a–b illustrates views of several embodiments of impellers (threads not shown) having magnets disposed in the substrate in various patterns.
Figure 10B:
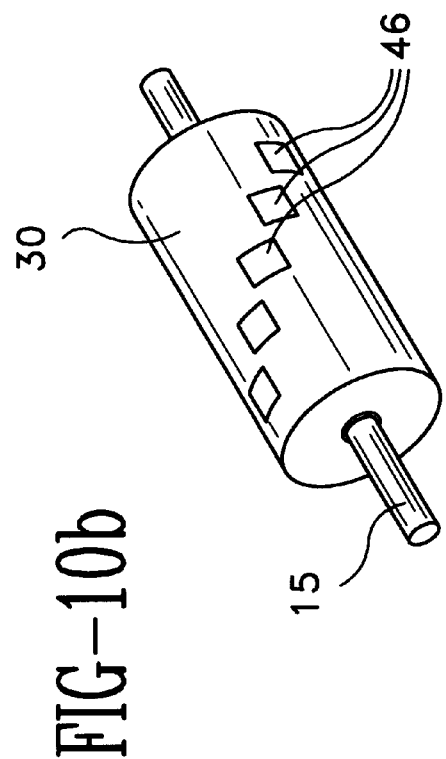

FIGS. 10a–b illustrate several embodiments of magnets 46 disposed in various patterns on or in the substrate of an impeller 30 (threads or appendages not shown on impeller). The magnets 46 may be disposed on or in the impeller 30 in a spiral pattern having a constant lead angle over the length of the impeller 30. The magnets 46 may be disposed in parallel rows or in a staggered pattern. Magnets 44 may be disposed in the magnetic surface 42 in a pattern duplicative of the lead angle of the magnets 46 in the impeller 30. The magnets 46 may be spaced apart or in strips. Additional patterns are envisioned.

Figure 11:
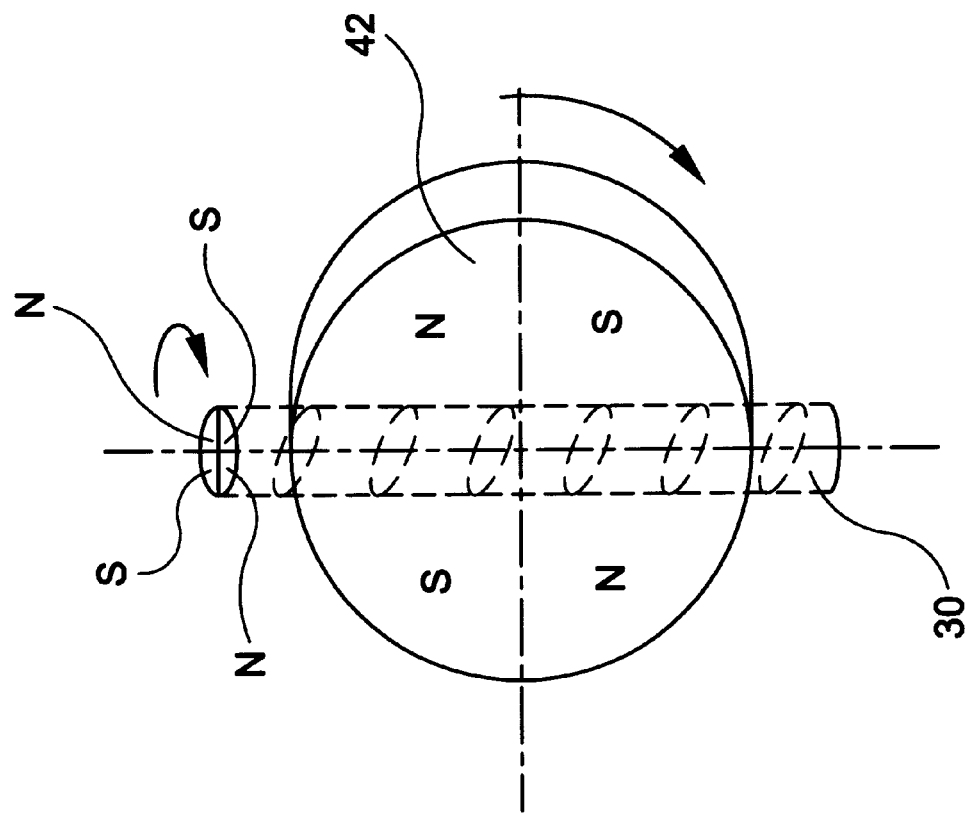
FIG. 11 illustrates a view of an external magnetic drive system superimposed over an impeller disposed in a catheter (not shown) in a body lumen.

FIG. 11 illustrates a magnetic surface 42 superimposed over an impeller 30 which is disposed in a catheter (not shown) in a body vessel. The back of the magnetic surface 42 has opposite polarity. The magnetic surface 42 shown is made of 4 quadrants of magnetic material. The face of the magnetic surface 42 oriented toward the impeller is made of wedges that alternate north and south in polarity. The preferred axis of the magnetic surface 42 shown is about 90 degrees to the axis of the impeller 30. The impeller 30 may be quartered into alternating north and south polarities which run along the longitudinal axis of the impeller 30. The substrate of the impeller 30 may be magnetized and the threads may not be magnetized. When the magnetic surface 42 rotates, the external north magnet engages the internal south magnet, and the external south magnet engages the internal north magnet resulting in rotation of the impeller 30.

Figure 12:
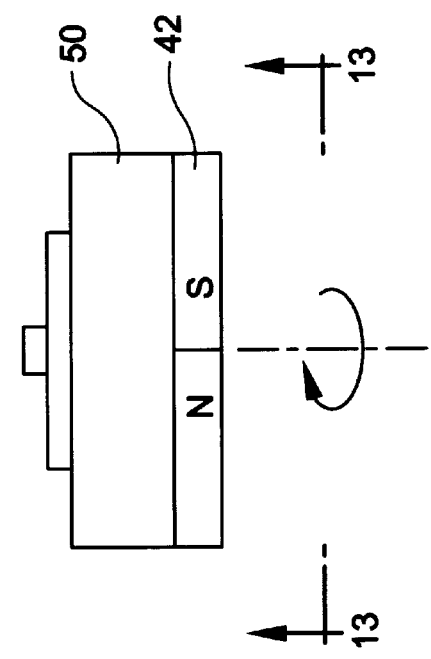
FIG. 12 illustrates a side view of the external magnetic drive system having a magnetic surface.

FIG. 12 illustrates a side view of an embodiment of a magnetic drive system 50 magnetic surface 42 having alternating north and south magnets embedded in the bottom surface.

Figure 13:
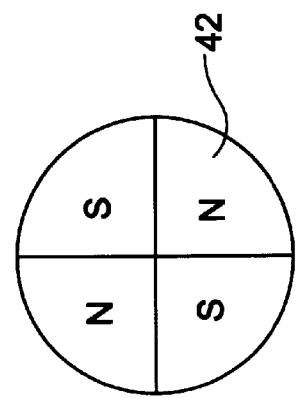
FIG. 13 illustrates a bottom view of the magnetic surface of FIG. 12 having alternating polarity.

FIG. 13 illustrates a bottom view of the magnetic surface 42 of FIG. 12 showing the alternating north and south polarized magnets.

Figure 14:
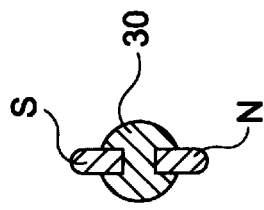
FIG. 14 illustrates a cross-section of an impeller showing magnetized helical threads with north and south polarity disposed in a non-magnetized substrate or shaft.

FIG. 14 illustrates a cross-sectional view of an end of the impeller 30 having two magnetic threads which are helically disposed about a non-magnetized substrate or shaft. The substrate is not magnetized and the threads are magnetized. Continuous threads of magnetized material (north or south) extend from the substrate. One thread is magnetized north and the other thread is magnetized south. The external north magnet of a magnetic surface 42 magnetically couples with the internal south magnets of the impeller 30 and the external south magnet magnetically couples with the internal north magnet.

Figure 15:
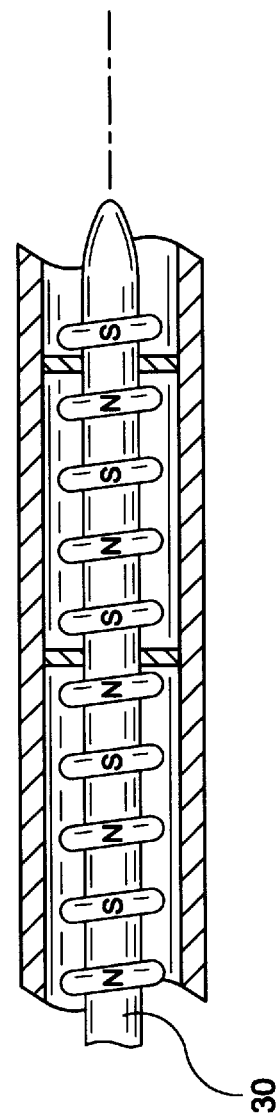
FIG. 15 illustrates a side view of an impeller with threads having alternating polarity.

FIG. 15 shows a side view of an impeller 30 having threads with alternating polarity.

Figure 16:
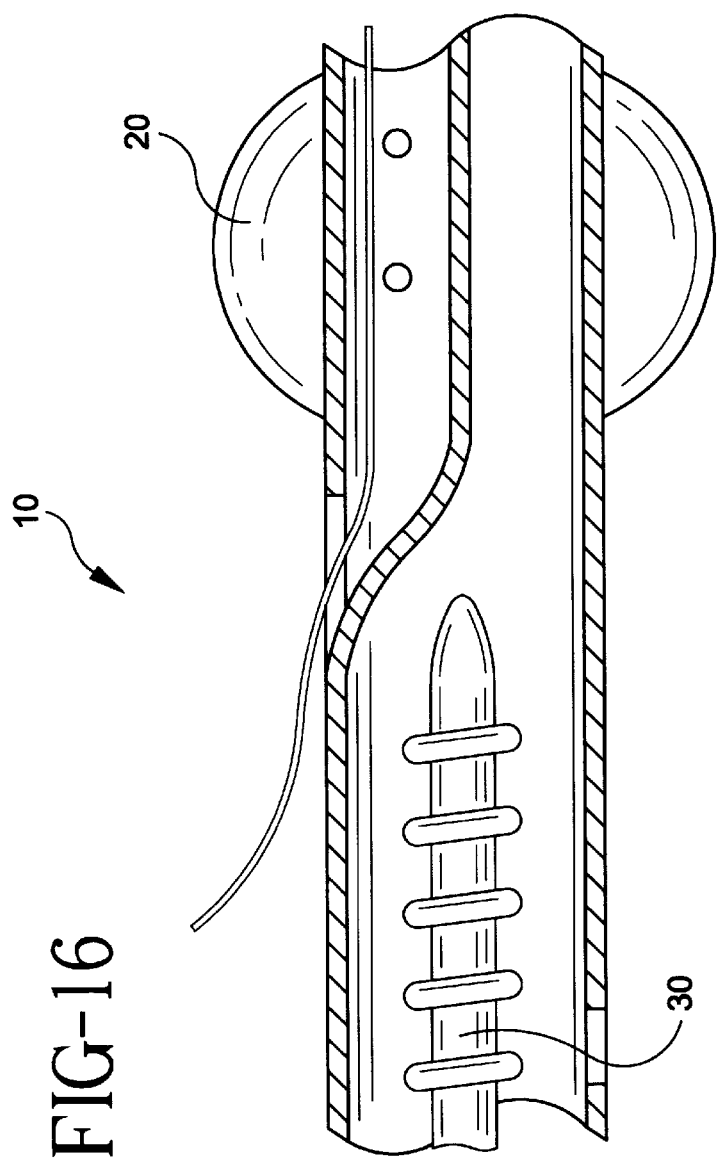
FIG. 16 illustrates a rapid exchange embodiment of the perfusion catheter.

FIG. 16 illustrates a rapid exchange embodiment of the perfusion catheter 10 having trilumens, apertures, impeller, balloon, and guidewire.

Figure 17:
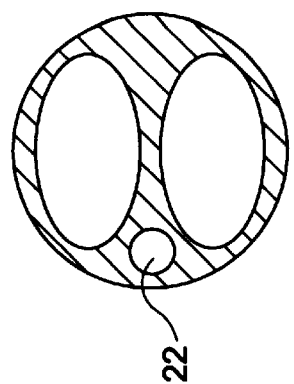
FIG. 17 illustrates a cross-sectional view of the catheter of FIG. 16 showing a balloon inflation lumen, rapid exchange lumen, and active perfusion lumen.

FIG. 17 illustrates a cross-section of the catheter 10 of FIG. 16 showing a balloon inflation lumen, rapid exchange lumen, and active perfusion lumen.

FIG. 18 illustrates a coaxial to bitumen embodiment of the perfusion catheter 10 having lumens, apertures, impeller, balloon, and guidewire. Ports for contrast used to inflate the balloon are located on the other side from the segment for the guidewire. The contrast lumen is plugged at the distal portion of the catheter 10.

FIG. 19 illustrates a cross-section of the catheter 10 of FIG. 18 showing a contrast lumen, guidewire lumen and perfusion lumen.

It will be evident from considerations of the foregoing that the perfusion balloon catheter is now available, and may be constructed using a number of methods and materials, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. A perfusion balloon catheter comprising:
    a first shaft having proximal and distal portions, a wall, one or more first apertures through the wall, a balloon disposed on the shaft distal of the first apertures,
    an inflation lumen in communication with the balloon, and a perfusion lumen in communication with the first apertures;
    at least one impeller disposed in the perfusion lumen, the impeller having a predetermined shape and one or more magnets disposed thereon, the magnets adapted to magnetically couple with a magnetic source spaced away from the perfusion balloon catheter and adapted to cause rotation of the impeller and
    a second shaft disposed in the first shaft, through the impeller, and extending distal thereof, the second shaft having proximal and distal portions and a wall, the wall having one or more apertures in the distal portion of the second shaft, and one or more apertures distal of the impeller, a perfusion lumen disposed in the second shaft between the apertures and being in communication therewith.

2. The perfusion balloon catheter of claim 1 wherein rotation of the impeller conveys fluid through the perfusion lumen.

3. The perfusion balloon catheter of claim 1 wherein the impeller is located distal of the first apertures.

4. The perfusion balloon catheter of claim 1 wherein the impeller is disposed under a portion of the balloon.

5. The perfusion catheter system of claim 1 wherein the impeller is made of at least one of metal, ceramic, or polymeric material.

6. The perfusion catheter system of claim 1 wherein the impeller includes at least one spiral-shaped groove.

7. The perfusion balloon catheter of claim 1 wherein the impeller includes at least one rib, thread, or screw.

8. The perfusion balloon catheter of claim 1 wherein the impeller is adapted to operate like an archimedes screw.

9. The perfusion balloon catheter of claim 1 further comprising an external magnetic drive system adapted to provide a magnetic field to a vicinity of the magnets on the impeller.

10. The perfusion balloon catheter of claim 1 wherein the impeller further comprises a plurality of magnets disposed thereon to collectively form a continuous spiral magnet.

11. The perfusion balloon catheter of claim 1 wherein the impeller includes a plurality of magnets disposed side-by-side to form a generally continuous magnetic thread, each magnetic thread having an opposite magnetic polarity at its outer extremity to its adjacent magnetic thread, the impeller adapted to rotate by exposing at least one magnetic thread to successive magnetic drive magnets of the opposite polarity upon rotation of the magnetic drive wherein successive magnetic coupling between the magnetic thread and the successive magnetic drive magnets rotates the impeller.

12. The perfusion balloon catheter of claim 1 further comprising
    an external magnetic drive system including a magnetic surface adapted to generate a magnetic field to one or more magnets disposed on a component connected to the impeller causing a magnetic coupling and rotation of the impeller.

13. The perfusion balloon catheter of claim 12 wherein the external magnetic drive system is powered by a source selected from a battery, electricity, magnetic coupling, or combination thereof.

14. A perfusion catheter system comprising:
    a drive system comprising an elongated shaft having at least one magnetic surface comprising a plurality of first magnets disposed thereon, the magnetic surface adapted to rotate and be disposed on or adjacent a body surface;
    a catheter less than 15 French in size having proximal and distal ends, one or more lumens longitudinally disposed therein, one or more supports mounted in the lumen, and an elongated impeller having one or more second magnets disposed thereon; and the drive system adapted to rotate causing successive magnetic coupling between the first magnets and the second magnets and rotation of the impeller.

15. The perfusion catheter system of claim 14 wherein the first magnets are magnetically attracted to the second magnets of the opposite polarity and magnetically couple, the rotation of the magnetic surface exposing the second magnets to different first magnets of the opposite polarity which are disposed further along the length of the magnetic surface, such that the second magnets are magnetically coupled to different first magnets as the shaft rotates causing the impeller to rotate and fluid to move in the catheter.

16. A method of actively perfusing blood through a catheter comprising the steps of:

inserting a shaft into a body lumen, the shaft having proximal and distal portions, a wall, one or more first apertures in the wall, and at least one perfusion lumen disposed distal of the first apertures and being in communication therewith, the perfusion lumen having at least one impeller disposed rotateably therein, wherein the impeller includes a plurality of magnets disposed generally side-by-side to form generally continuous magnetic thread, each magnetic thread having an opposite magnetic polarity at its outer extremity to its adjacent magnetic thread, the impeller adapted to rotate and convey blood through one of the first apertures and through the perfusion lumen upon application of a magnetic force thereto; and applying a magnetic field from a magnetic drive system external to the impeller and the body lumen by exposing at least one magnetic thread to successive magnetic drive magnets of the opposite polarity by rotating the magnetic drive so that successive magnetic coupling between the magnetic thread and the successive magnetic drive magnets rotates the impeller.

17. A perfusion balloon catheter comprising:

a first shaft having proximal and distal portions, a wall, one or more first apertures through the wall, a balloon disposed on the shaft distal of the first apertures, an inflation lumen in communication with the balloon, and a perfusion lumen in communication with the first apertures; and at least one impeller disposed in the perfusion lumen, the impeller having a predetermined shape and one or more magnets disposed thereon, wherein the magnets are disposed side-by-side to format generally continuous magnetic thread, each magnetic thread having an opposite magnetic polarity at its outer extremity to its adjacent magnetic thread, the impeller adapted to rotate by exposing at least one magnetic thread to successive magnetic drive magnets of the opposite polarity upon rotation of the magnetic drive wherein successive magnetic coupling between the magnetic thread and the successive magnetic drive magnets rotates the impeller.

* * * * *